(12) United States Patent
Ulbrich et al.

(10) Patent No.: US 8,052,928 B2
(45) Date of Patent: Nov. 8, 2011

(54) TISSUE INFILTRATION APPARATUS

(75) Inventors: Hermann Ulbrich,
Bad-Schönborn-Mingolsheim (DE);
Karl-Heinz Westerhoff,
Eppingen-Elsenz (DE); Stefan Künkel,
Karlsruhe (DE); Janet I. Minshew,
Libertyville, IL (US)

(73) Assignee: Leica Biosystems Nussloch GmbH,
Nussloch (DE)

( * ) Notice: Subject to any disclaimer, the term of this patent is extended or adjusted under 35 U.S.C. 154(b) by 236 days.

(21) Appl. No.: 12/031,800

(22) Filed: Feb. 15, 2008

(65) Prior Publication Data

US 2008/0199955 A1    Aug. 21, 2008

(30) Foreign Application Priority Data

Feb. 20, 2007   (DE) .................. 10 2007 008 713

(51) Int. Cl.
*G01N 21/00* (2006.01)

(52) U.S. Cl. ............ 422/65; 422/63; 422/64; 422/66; 422/67; 422/500; 422/501; 436/180

(58) Field of Classification Search ............ 422/63–67, 422/99–100, 500–501; 436/180
See application file for complete search history.

(56) References Cited

U.S. PATENT DOCUMENTS

| | | | |
|---|---|---|---|
| 4,113,436 A | | 9/1978 | Werder et al. |
| 5,601,650 A | * | 2/1997 | Goldbecker et al. .......... 118/697 |
| 6,058,788 A | | 5/2000 | Thiem et al. |
| 6,436,348 B1 | * | 8/2002 | Ljungmann et al. ............ 422/63 |
| 6,594,537 B1 | | 7/2003 | Bernstein et al. |
| 7,075,045 B2 | | 7/2006 | Visinoni |
| 2002/0098118 A1 | * | 7/2002 | Eckert et al. .................... 422/65 |
| 2002/0182049 A1 | | 12/2002 | Gutig |
| 2003/0092186 A1 | | 5/2003 | Pressman et al. |
| 2004/0002163 A1 | | 1/2004 | Reinhardt et al. |
| 2005/0002830 A1 | | 1/2005 | Fredenburgh |
| 2005/0059155 A1 | | 3/2005 | Graupner et al. |

FOREIGN PATENT DOCUMENTS

| | | |
|---|---|---|
| DE | 4032048 C2 | 4/1992 |
| WO | 9323732 A1 | 11/1993 |
| WO | 2005031312 A1 | 4/2005 |

* cited by examiner

*Primary Examiner* — Jyoti Nagpaul
(74) *Attorney, Agent, or Firm* — Hodgson Russ LLP

(57) ABSTRACT

A tissue infiltration apparatus (1) for specimens present in cassettes (5). comprises at least two liquid containers (7, 11, 13, 15) and a transport apparatus (6). A liquid having a definable property is introducible into a liquid container (7, 11, 13, 15). Multiple cassettes (5) are receivable in a transport basket (4). The transport apparatus (6) is configured in such a way that with it, at least two transport baskets (4) are transportable in the tissue infiltration apparatus (1). A transport basket (4) is deliverable to a liquid container (7, 11, 13, 15) and/or movable away from a liquid container (7, 11, 13, 15) with the transport apparatus (6). An execution sequence (21) in which the transport baskets (4) pass through the liquid containers (7, 11, 13, 15) of the tissue infiltration apparatus (1) is definable. To enable accelerated or preferred processing of a transport basket (4) with the tissue infiltration apparatus (1), but without using an additional liquid container provided only for that purpose, at least one means (8) is provided with which the order of two transport baskets (4) is definably modifiable.

13 Claims, 3 Drawing Sheets

TISSUE INFILTRATION APPARATUS

CROSS REFERENCE TO RELATED APPLICATIONS

This application claims priority of German patent application no. 10 2007 008 713.8 filed Feb. 20, 2007, which is incorporated herein by reference.

FIELD OF THE INVENTION

The present invention relates to a tissue infiltration apparatus for specimens present in cassettes. The tissue infiltration apparatus encompasses at least two liquid containers and a transport apparatus. A liquid having a definable property is introducible into a liquid container, also called a retort. Multiple cassettes are receivable in a transport basket. The transport apparatus is configured in such a way that with it, at least two transport baskets are transportable in the tissue infiltration apparatus. A transport basket is deliverable to a liquid container and/or movable away from a liquid container with the transport apparatus. An execution sequence in which the transport baskets pass through the liquid containers of the tissue infiltration apparatus is definable or defined.

BACKGROUND OF THE INVENTION

Tissue specimens for histological examinations are prepared by means of multiple chemical treatments and a final embedding of the specimen in paraffin. In the chemical treatment, the specimen is first fixed with a suitable chemical liquid, and then the water contained in the specimen is removed and is then replaced with stabilizers, dyes, and the like. Lastly, the specimen is embedded in paraffin or wax. The result is that a paraffin block can be held in stable fashion in a receptacle of a microtome for the cutting of individual thin tissue sections. So-called tissue infiltration apparatuses or automatic embedders, which automatically transport the specimens into the various treatment phases, were developed for the various method steps proceeding in succession.

A specimen can be tissue or body fluids from humans or various species of animals, plants, or insects and will vary in size from small biopsies to whole organs to whole bodies. Specimens are processed with the objective that a diagnosis will be rendered after thin sections of the specimen are stained and examined microscopically to determine cellular morphology, chemical composition and the function of normal and abnormal tissue. These specimens are each introduced into a cassette, in which they are transported through the individual treatment steps. Reference is made, purely by way of example, to DE 103 42 264 A1 which describes, inter alia, such a cassette. These specimens, or thin tissue sections thereof, are ultimately intended to be conveyed for histological examination. For this, a pathologist views, with the aid of a microscope, a specimen section prepared with a microtome and placed onto a specimen slide; the specimen section can be stained with a staining method and provided with a coverslip.

The transport apparatus of the tissue infiltration apparatus is intended in particular to make it possible to transport at least two transport baskets simultaneously in the tissue infiltration apparatus, or to transport two transport baskets, present simultaneously in the tissue infiltration apparatus, in succession with a time offset. As a rule, a transport basket is brought to a liquid container and into it using the transport apparatus. With the transport apparatus the transport basket is then, usually at a later point in time, moved out of a liquid container and away from the liquid container.

An "execution sequence" or "processing order" for purposes of the present invention is to be understood in particular to mean that an order in which a transport basket having cassettes passes through the liquid containers provided in the tissue infiltration apparatus is predefined or can be predefined (for example by an operator of the tissue infiltration apparatus). A liquid container can also be construed here as a processing station at which the cassettes (and therefore specimens) present in a transport basket are introduced into the liquid provided in the liquid container, with the result that the liquid acts on the specimens. In this context, the term "pass through" is to be understood for purposes of the present invention, in particular, as follows:

delivery of a transport basket, having cassettes and accordingly having specimens, from an input station, at which a transport basket is transferred to the tissue infiltration apparatus, to and into the first liquid container in the execution sequence;

removal from the liquid container after a definable contact time;

delivery of a transport basket to and into the next liquid container, etc.; and lastly delivery to an output or transfer station at which a processed transport basket can be outputted or removed from the tissue infiltration apparatus.

DE 196 47 662 C1, for example, discloses a tissue infiltration apparatus in which a plurality of liquid containers are arranged in circular fashion. One, and in some circumstances also multiple, transport baskets can be transferred successively in time-offset fashion to this tissue infiltration apparatus. These baskets are conveyed by the transport apparatus provided therein, in a predefined rotation direction, from one liquid container to the next; the transport apparatus provided therein is configured in such a way that in the context of a transport operation, all the transport baskets present in the tissue infiltration apparatus are delivered to the respective next liquid container. One complete pass by a transport basket can require one to several hours. Fully automated tissue infiltration apparatuses can, when appropriately loaded, be operated automatically overnight. As soon as one transport basket is transferred to the tissue infiltration apparatus, a further transport basket can be transferred to the tissue infiltration apparatus, but it is transported and thus processed sequentially, through the individual stations or liquid containers of the tissue infiltration apparatus, in the same execution sequence as the transport basket already present in the tissue infiltration apparatus. If the specimens present in a transport basket need to be processed in particularly urgent fashion, this is not readily possible with the tissue infiltration apparatus known from DE 196 47 662 C1, since transport baskets already present in the tissue infiltration apparatus cannot readily be removed prior to a complete pass through the tissue infiltration apparatus.

This problem is addressed in DE 101 63 488 A1, which provides a tissue infiltration apparatus that comprises an additional liquid container having a smaller fill volume than the first treatment chamber. Multiple transport baskets are processed in the first treatment chamber. In the additional liquid container, a transport basket can be subjected to urgent processing. In this context, the liquid necessary for the particular processing step is respectively introduced into said liquid container and, after a predefined contact time, drained again. This enables a transport basket to be subjected to an urgent tissue infiltration, but it is also necessary, once the liquid container has been drained, firstly to clean it before it can be filled with another liquid. This in turn is complex, and requires complex controlling of the filling and draining operations and of the liquid container and the first treatment chamber. Cleaning reagents must additionally be used, thus increasing operating costs for the tissue infiltration apparatus.

SUMMARY OF THE INVENTION

It is therefore the object of the present invention to describe and further develop a tissue infiltration apparatus that overcomes the disadvantages set forth above. The tissue infiltration apparatus is intended, in particular, to make possible accelerated or preferred processing of a transport basket, but without using an additional liquid container provided solely for that purpose.

The tissue infiltration apparatus according to the present invention of the kind cited initially achieves the aforesaid object by way of a tissue infiltration apparatus of this kind characterized in that at least one means is provided with which the order of two transport baskets is definably modifiable.

The modification of the order of two transport baskets refers in particular to the execution sequence or processing order of the transport baskets passing through the tissue infiltration apparatus.

What has been recognized according to the present invention is firstly that the object stated initially can be achieved, for example, in that the transport apparatus is configured in such a way that the order in which the transport baskets pass through the tissue infiltration apparatus can be modified with respect to one another. The result is that, for example, a transport basket requiring fast processing can "overtake" a transport basket already present in the tissue infiltration apparatus, so that it has passed through the predefined processing program earlier. The transport basket requiring fast processing can thus also be outputted from the tissue infiltration apparatus earlier than the transport basket that was introduced previously into the tissue infiltration apparatus and has been overtaken. With this action, it is not necessary to provide a further liquid container that must be filled with liquids or chemicals and drained, and with which the transport basket requiring fast processing must be processed, so to speak, in an independent, autonomous execution program. Instead, according to the present invention, the one liquid container of the tissue infiltration apparatus that is present in any case can be utilized, and as a rule it is also not necessary to fill one or more liquid containers with other liquids or chemicals, in a manner deviating from a normal procedure for the tissue infiltration apparatus, in order to process an "urgent" transport basket more quickly with the tissue infiltration apparatus. The means for modifying the order of the transport baskets could thus be constituted by the fact that only the transport apparatus can bring about such a modification of the order of the transport baskets. One example of this would be a "switching station" in which two transport baskets that are in a transport operation and are arranged one behind another can be exchanged in terms of their order. Alternatively or in addition thereto, a storage unit could be provided in which at least one transport basket can be stored or temporarily held while another transport basket is transferred to a position that is ahead in the order of transport baskets.

In a very particularly preferred embodiment, three liquid containers are provided, into each of which a transport basket is introducible. Corresponding liquids are introduced into these liquid containers. A transport basket can be introduced into such a liquid container, with the result that the cassettes received by the transport basket are immersed into the liquid so that the liquid acts on the cassettes and on the specimens. The three liquid containers could usefully be filled with liquids that are suitable respectively for fixing, for dehydrating, and for wax/paraffin treatment of the specimens. These three liquid containers thus represent three processing stations of the tissue infiltration apparatus, which are passed through successively and which represent, in terms of the chemical process occurring respectively therein, a useful subdivision of the fundamental processing steps of the tissue infiltration apparatus that are to be performed. This subdivision is useful because, among other reasons, the processing time for fixing, dehydration, and wax/paraffin treatment of the specimens accounts in each case for approximately one-third of the total processing time. The cycle change time in accordance with which a transport basket is delivered from one liquid container to another liquid container would accordingly correspond to one-third of the total processing time. It is thus also possible in this context to introduce a transport basket requiring fast processing into the tissue infiltration apparatus and perform the modification or transposition of the order of the transport baskets, in particular in the context of a stipulated cycle change.

As already indicated, one liquid container could serve for fixing the specimens present in the cassettes and could be fillable for that purpose with a liquid suitable for fixing. One liquid container could serve for dehydration of the specimens present in the cassettes and could be fillable for that purpose with at least one liquid suitable for dehydration. A further liquid container could serve for wax/paraffin treatment of the specimens present in the cassettes and could be fillable for that purpose with at least one liquid suitable for wax/paraffin treatment.

In a very particularly preferred embodiment, the means for modifying the order of the transport baskets comprises at least one storage unit. This storage unit is embodied in such a way that at least one transport basket, by preference up to six transport baskets, is/are storable in it. In the simplest case, a storage unit of this kind could be constituted by an area in which one or more transport baskets are "parked" or temporarily held. The storage unit could also be embodied in the form of a carousel that comprises multiple receiving positions, for example two to six receiving positions. A transport basket can be received in one such receiving position so that it can be temporarily held in the storage unit. If the transport apparatus implements only one substantially linear forward motion direction, the storage unit embodied in the form of a carousel could be provided at one point in this transport path. If necessary, a transport basket is transferred into the storage unit at a transfer position. By rotation of the carousel, a further receiving position of the storage unit can be transferred to the transfer position location so that a further transport basket can be transferred to the storage unit. If a transport basket present in the storage unit then needs to be delivered from the storage unit to a liquid container, the carousel must be rotated in such a way that the receiving position of the transport basket is brought to the transfer position, so that the transport apparatus can remove the transport basket from the storage unit.

The order of two transport baskets could in principle be modified or transposed with the aid of the transport apparatus, for example in an operating state in which two transport baskets are being transported substantially simultaneously in the tissue infiltration apparatus. A transposition module, in which transposition of the order of two transport baskets takes place, could be provided for this. For example, the transport apparatus could comprise a rail system on which multiple gripping arms are guided. The transposition module (along the lines of a switching station) could be provided at a definable location in the rail system; in said module, two gripping arms each equipped with a transport basket are introduced, and the order of the gripping arms plus transport baskets can be transposed.

According to a preferred embodiment, the order of two transport baskets is modified in such a way that a first transport basket is deliverable from a present position in the tissue infiltration apparatus to the storage unit. Another transport basket is then delivered to the position at which the first transport basket was located. The other transport basket could also be delivered to a position in the tissue infiltration apparatus that is downstream, in terms of the execution sequence, from the current position of the first transport basket. Provision could even be made, optionally, to skip a processing station or a liquid container if necessary.

The storage unit could be configured, for example, in the form of a parking area, i.e. one where the transport baskets are merely parked and optionally can be stored at a definable temperature or under definable environmental conditions. A storage unit of this kind could be provided, for example, if the transport apparatus comprises one or more robot arms, so that a transport basket parked at a definable position in the parking area can also be picked up again by a robot arm. Alternatively, a storage unit can comprise a carousel storage unit. This is an assembly that comprises multiple—for example, six—receiving spaces into each of which a transport basket can be placed. The carousel storage unit can be embodied rotatably about an axis, so that the carousel storage unit comprises a transfer position at which a transport basket can be transferred to or removed from the carousel storage unit. A storage unit of this kind could be used in the context of a transport apparatus that comprises a rail system that has gripping arms and with which a transport basket can always be picked up or parked at a definable position.

Concretely, the storage unit could be arranged at one of the liquid containers. The storage unit could be in operative engagement with the liquid container, said engagement being provided, for example, by the transport apparatus. In this case provision could be made, for example, for a transport basket to be delivered into the storage unit only once said basket has already been treated in the liquid container. The storage unit is preferably arranged at the liquid container for fixing.

According to a very particularly preferred embodiment, a control device is provided with which control is applicable to the transport apparatus and/or to components of the tissue infiltration apparatus. With the control device, control could thus be applied to the transport apparatus in such a way that the transport baskets to be processed by the tissue infiltration apparatus are each transported in a definable execution sequence or order through the liquid containers and optionally to or from the storage unit. The control device could be embodied in such a way that an individual execution sequence can be implemented for each transport basket. Control is applicable by the control device, in particular, to a filling and/or draining unit of at least one liquid container. These could be liquid pumps and/or valves.

There are various ways of advantageously embodying and refining the teaching of the present invention. The reader is referred, for that purpose, to the specification including without limitation the explanation below of the preferred exemplifying embodiments of the invention with reference to the drawings. In conjunction with the explanation of the preferred exemplifying embodiments of the invention with reference to the drawings, an explanation is also given of generally preferred embodiments and refinements of the teaching.

BRIEF DESCRIPTION OF THE DRAWING VIEWS

In the drawings, schematically in each case:

DETAILED DESCRIPTION OF THE INVENTION

Figure 1:
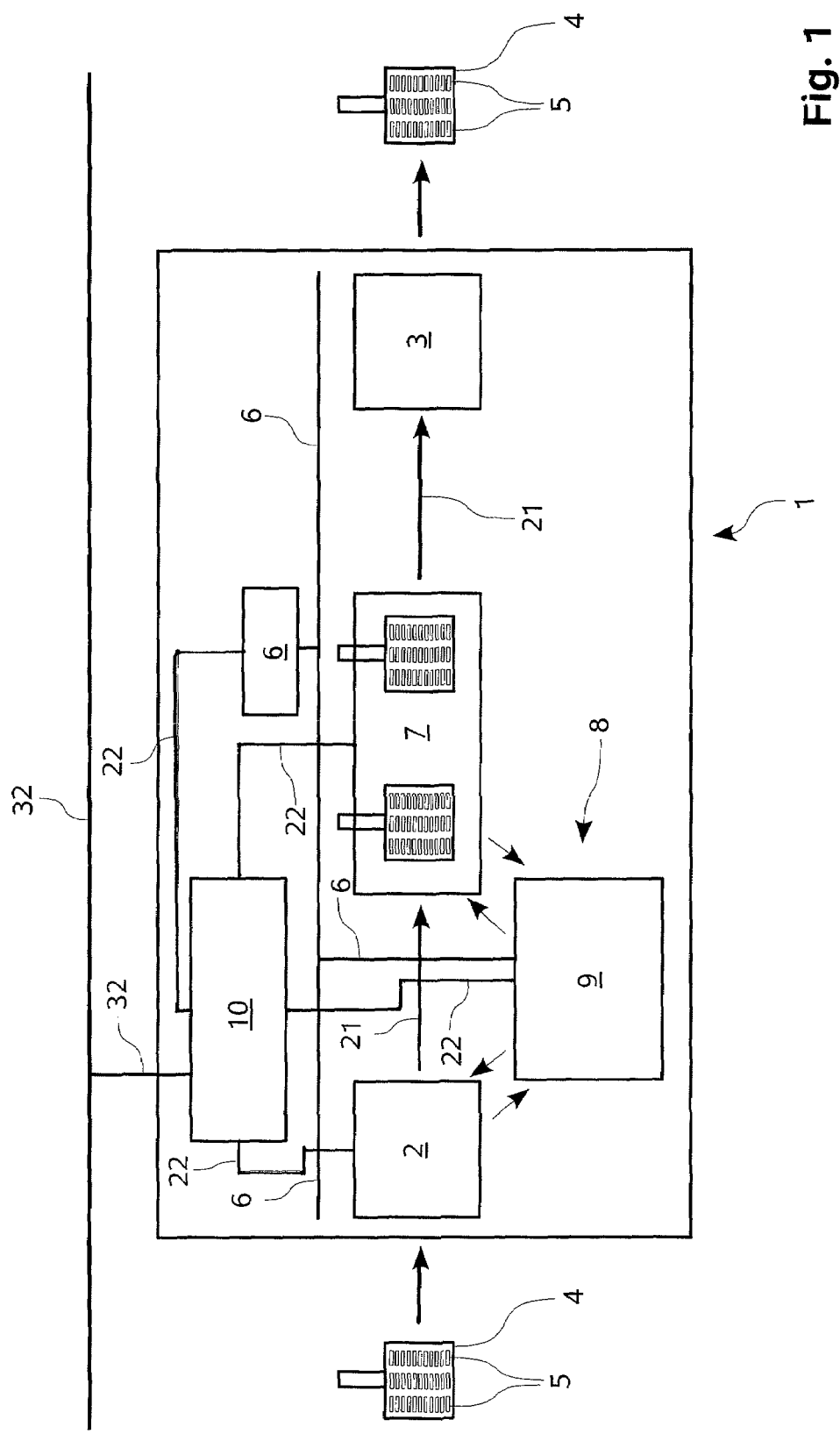
FIG. 1 shows a first exemplifying embodiment of a tissue infiltration apparatus according to the present invention.

In the Figures, identical or similar components or assemblies are labeled with the same reference characters.

FIG. 1 shows a first exemplifying embodiment of a tissue infiltration apparatus 1 according to the present invention. Tissue infiltration apparatus 1 comprises an input station 2 and an output station 3. An operator can transfer a transport basket 4 to input station 2 of tissue infiltration apparatus 1. In comparable fashion, an operator can remove from output station 3 a transport basket 4 that has passed through tissue infiltration apparatus 1. It is indicated only schematically that multiple cassettes 5 can be received by a transport basket 4, specifically (in the exemplifying embodiment according to FIG. 1) up to sixty cassettes 5 per transport basket 4.

Tissue infiltration apparatus 1 according to FIG. 1 further comprises a transport apparatus 6 with which a transport basket 4 can be transported within tissue infiltration apparatus 1, specifically from input station 2 to output station 3. Also indicated, only schematically, is the fact that tissue infiltration apparatus 1 comprises liquid containers 7 into which a transport basket 4 can be introduced. Concretely, there are two or three separate liquid containers.

Very generally, the transport apparatus 6 could comprise means for moving a transport basket or multiple transport baskets. A transport apparatus 6 could therefore comprise elements for grasping a transport basket. It is also conceivable for a transport basket 4 to be hooked into a correspondingly embodied element of the transport apparatus 6. In addition, means could be provided with which such a gripping or hooking element can be moved on and/or moved vertically. For this purpose, a rail system could be used in combination with telescoping elements. In very particularly preferred fashion, however, the transport apparatus 6 comprises at least one robot arm with which at least one transport basket can be transported or moved in the tissue infiltration apparatus 1. A robot arm of this kind could comprise a gripping or hooking element that can be moved in a vertical and/or horizontal direction via an arm structure with a housing part of the tissue infiltration apparatus. A transport basket can thus be lifted, moved in a horizontal direction, and set down or introduced into a liquid container. The robot arm or transport apparatus could be embodied in such a way that a transport basket is transportable out of the tissue infiltration apparatus 1. With such a transport apparatus, a transport basket can be conveyed or transferred to a further processing device. It is also conceivable that with the transport apparatus, the transport baskets passing through the tissue infiltration apparatus are placed in an output area of the tissue infiltration apparatus. Similarly, with the transport apparatus, transport baskets could also be picked up from outside the tissue infiltration apparatus and transferred into it.

According to the present invention, a means 8 is provided with which the order of two transport baskets 4 is definably modifiable. This means 8 is configured, in the context of tissue infiltration apparatus 1, in the form of a storage unit 9. A transport basket 4 can accordingly be delivered from input unit 2 or from a liquid container 7 to storage unit 9. The result is that, so to speak, a path is cleared for another transport basket 4 that was arranged, with respect to execution sequence 21 of transport baskets 4 in tissue infiltration apparatus 1, behind the transport basket 4 delivered into storage unit 9.

Tissue infiltration apparatus 1 furthermore comprises a control device 10 with which control can be applied to transport apparatus 6. Control unit 10 is connected to transport apparatus 6, to input station 2, to storage unit 9, and to liquid containers 7 for information exchange and for application of control to these components via control leads 22.

Figure 2:
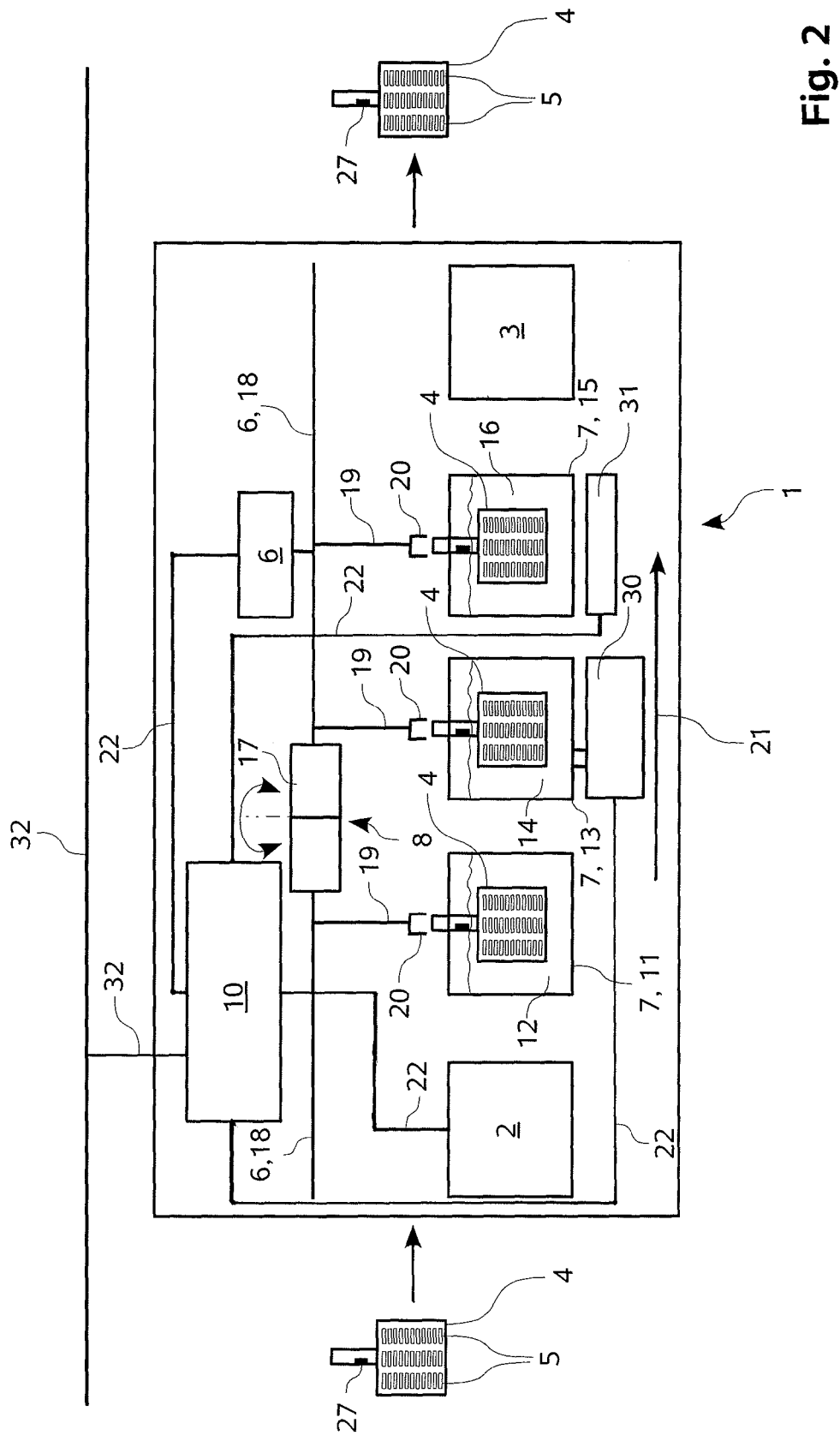
FIG. 2 shows a second exemplifying embodiment of a tissue infiltration apparatus according to the present invention.

FIG. 2 shows a second exemplifying embodiment of a tissue infiltration apparatus 1 according to the present invention. Tissue infiltration apparatus 1 shown in this Figure also comprises an input station 2, an output station 3, a transport apparatus 6, and liquid containers 7. Concretely, three liquid containers 7 are provided. Liquid container 11 serves for fixing the specimens and is filled for that purpose with a liquid 12 suitable for fixing. Liquid container 13 serves for dehydration and is fillable with a liquid 14 suitable for that purpose. Liquid container 15 serves for paraffin treatment of the specimens and is fillable with a liquid 16 suitable for that purpose. Transport apparatus 6 is embodied in the form of a rail system and comprises rails 18 for that purpose. Transport arms 19 are guided movably on rails 18. A transport arm 19 comprises a coupling element 20 with which a transport basket 4 can be coupled to transport arm 19. In the operating state of tissue infiltration apparatus 1 shown in FIG. 2, a transport basket 4 is located in each of the three liquid containers 11, 13, and 15 of FIG. 2.

The liquid level of at least one liquid container and/or the fill volume of at least one liquid container could be definably adjustable, for example by way of a displaceable-height bottom of the liquid container. The result is that ultimately the effective liquid level of the liquid can be adapted to the particular processing step, with a consequent savings of liquid or chemicals.

In a very particularly preferred embodiment, the transport baskets pass, in accordance with a definable execution sequence, firstly through the liquid container for fixing, then the liquid container for dehydration, and then the liquid container for wax/paraffin treatment. The liquid containers provided for this purpose accordingly are correspondingly arranged, or are correspondingly populated by the transport apparatus with transport baskets, in said execution sequence.

Means 8 for modifying the order of transport baskets 4 is embodied in the form of a transposition module or switchover station 17. With it, two transport baskets that have each been picked tip by a transport arm 19 and are located one behind another in switchover station 17 are transposed in terms of order. Although transport apparatus 6 in FIG. 2 is based on rails 18 or on a rail system, a robot arm (not shown) could carry out transport of the transport baskets 4 within tissue infiltration apparatus 1.

Figure 3:
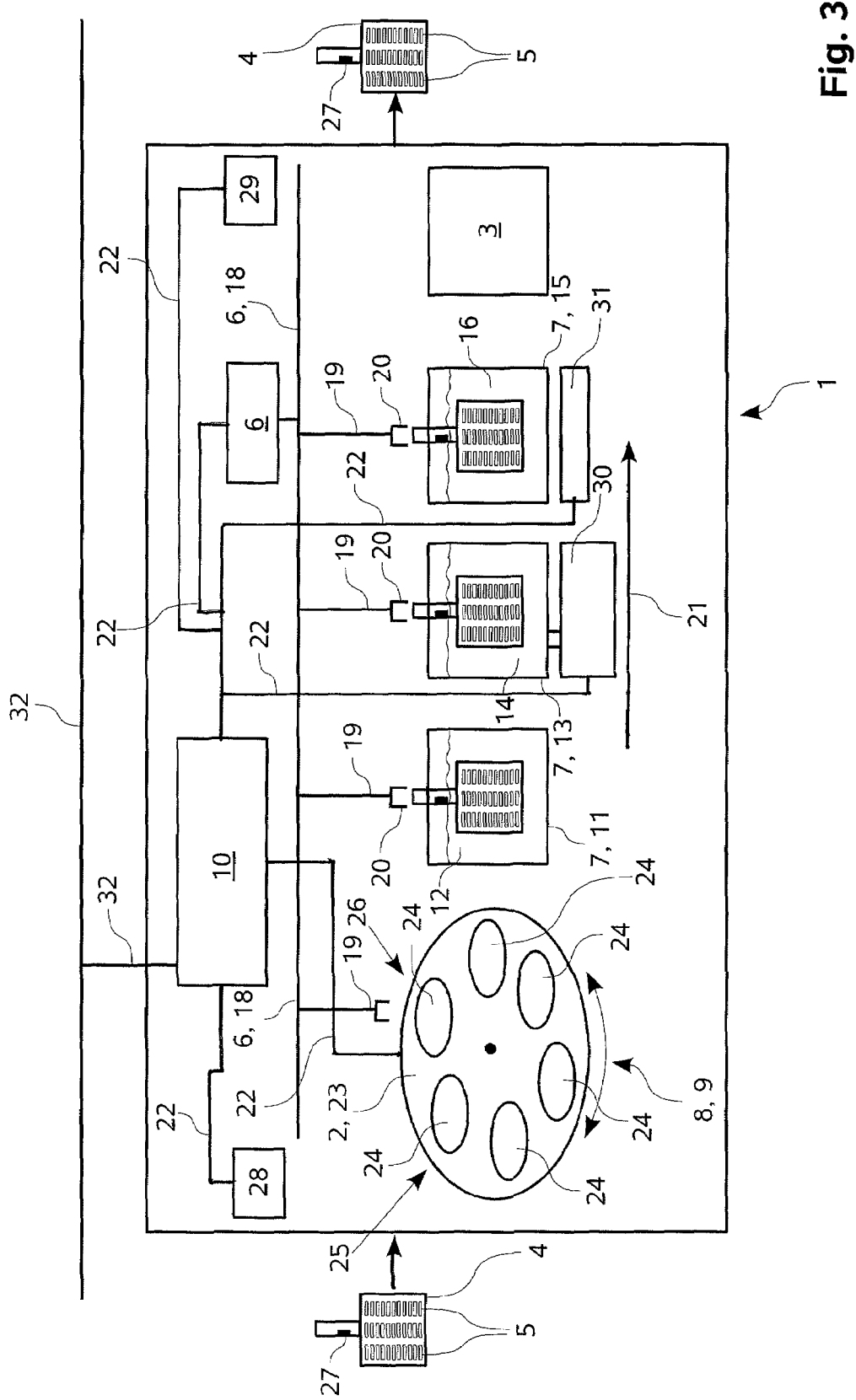
FIG. 3 shows a third exemplifying embodiment of a tissue infiltration apparatus according to the present invention.

FIG. 3 shows a further exemplifying embodiment of a tissue infiltration apparatus 1 according to the present invention, which differs from tissue infiltration apparatuses 1 shown in FIGS. 1 and 2 substantially in terms of a differently configured input station 2. The input station according to FIG. 3 is embodied in the form of a carousel 23 and serves simultaneously as a storage unit 9 and as means 8 for definable modification of the order of multiple transport baskets 4. Carousel 23 or storage unit 9 of FIG. 3 is substantially in operative engagement with liquid container 11. Carousel 23 comprises six individual receiving positions 24 into each of which a transport basket 4 can be placed. An operator transfers a transport basket 4 to tissue infiltration apparatus 1 by conveying it to input position 25, which is a receiving position 24 of carousel 23. At output position 26 of carousel 23, transport arm 19 (shown thereabove) can remove a transport basket 4 from the corresponding receiving position 24 and/or transfer to storage unit 9 or to carousel 23 a transport basket 4 that has already been processed in one of containers 11, 13, and/or 15. A transport basket 4 transferred to carousel 23 can be stored therein by the fact that carousel 23 rotates a different receiving position 24 to the input or output position 25, 26.

Let it be assumed that transport basket 4 shown at the left in FIG. 3 is to be placed, as a transport basket requiring urgent processing, into input position 25 of carousel 23. The three transport baskets 4 that are shown are located in liquid containers 11, 13, and 15. At the next station change of transport baskets 4, transport basket 4 present in liquid container 11 is delivered by transport arm 19 into output position 26 of carousel 23. Carousel 23 is then rotated one position to the right, so that transport basket 4 requiring urgent processing is delivered to output position 26. A transport arm 19 then delivers transport basket 4 into liquid container 11. At the next station change, the transport baskets present in liquid containers 11, 13, and 15 are then each moved one position further in execution sequence 21, and transport basket 4 that is still in carousel 23 can be delivered either back into liquid container 11 or, as soon as it is unoccupied, into liquid container 13. The result is that transport basket 4 requiring urgent processing has been brought one position ahead of the other transport basket 4 in execution sequence 21, so that the order of transport baskets 4 has been modified.

According to a preferred embodiment, the cassettes 5 and/or a transport basket 4 respectively comprise(s) an identifying means. The identifying means makes possible an identification of the cassettes and/or of the transport basket. The identifying means could be a barcode or a machine-readable imprint or a transponder or radio frequency identification (RFID) tag. Provision could be made that the present location or position of a cassette or of a transport basket within the tissue infiltration apparatus is ascertainable on the basis of the identifying means. The remaining treatment time of a cassette or of a transport basket could also be ascertainable on the basis of the identifying means. This feature can be helpful if a specimen or cassette must be accessed at an earlier time than expected, in which case the specimen can be processed manually.

The order of the transport baskets could be ascertainable, and optionally modifiable, as a function of the identification of the cassettes and/or the transport basket. In addition to the information concerning identification of the cassette or transport basket, information could also be provided regarding the type of processing of the specimens in the tissue infiltration apparatus, which information either is stored in suitable fashion in the identifying means or is transmitted, for example, via a network to the tissue infiltration apparatus, if identification of the respective cassette or transport basket is performed. A reading device, with which the identifying means of the cassettes or the transport basket can respectively be read, would need to be provided for this purpose in the tissue infiltration apparatus. This information could be conveyed to the control unit 10 of the tissue infiltration apparatus 1. The control unit 10 could be configured in such a way that as a function of the information ascertained for the cassettes or the particular transport basket, the execution sequence of the individual transport baskets (and thus of the cassettes) through the liquid containers of the tissue infiltration apparatus is managed in variable fashion, or in a manner optimized for a definable processing goal. One such processing goal could be a shortest possible processing time for the cassettes in the tissue infiltration apparatus. A further processing goal could be a special execution sequence for a specific type of specimen.

It is indicated merely schematically that the identifying means, embodied in the form of a transponder 27, is provided on each transport basket 4. Information about the identity of transport basket 4, as well as cassettes 5 and therefore the specimens (not shown) contained therein, can be stored in the identifying means. Information can additionally be stored in transponder 27 about the processing steps with which the samples are to be, or have been, processed. Information concerning prioritization of the processing of the individual specimens present in transport basket 4, or about transport baskets 4, can also be stored in transponder 27. The information stored in transponder 27 can be read out in non-contact fashion with reading unit 28, and transmitted to control unit 10. Control unit 10 can then, as a function of the information read out from transponder 27 of a transport basket 4, plan and correspondingly carry out the processing steps for that transport basket 4. Located in the vicinity of output station 3 is a writing unit 29 with which information about the individual processing steps that a transport basket 4 has passed through in tissue infiltration apparatus 1 can be written into transponder 27.

It is also conceivable for at least one liquid container to be fillable automatically with a different liquid. This could take place, in particular, at a definable or adjustable time. For example, the liquid container for dehydration could, in particular, be respectively filled with an alcohol-containing liquid having a different alcohol concentration. Additionally or alternatively, filling of the liquid container with a different liquid could be possible in operator-initiated fashion—manually, so to speak.

It is indicated merely schematically that liquid 14 of liquid container 13 serving for dehydration can be exchanged, for which purpose an exchange apparatus 30 is provided. The latter comprises pumps and valves (not illustrated), and is connected by means of two conduit connections to liquid container 13. Preferably, energy is applicable to the contents of at least one liquid container, in particular for a definable period of time. The energy is, in particular, thermal energy or electromagnetic waves, for example microwaves and/or ultrasonic waves. The contents of the liquid container to which heat or energy is to be applied could include the liquid, a transport basket present therein, and/or cassettes present therein. It is particularly useful to apply energy to the liquid container that is provided for wax/paraffin treatment, since this operation is thereby accelerated. Provided on liquid container 15 is a heating unit 31, embodied in the form of a microwave, with which liquid 16 in liquid container 15, and therefore also specimens 5, can be acted upon by thermal energy. The paraffin treatment operation can thereby be accelerated.

Very particularly preferably, provision is made that priority criteria, on the basis of which the order of the transport baskets is ascertainable, are inputtable and/or ascertainable. The priority criteria could be inputted, for example, by an operator. It is additionally conceivable that the priority criteria are transmitted to the tissue infiltration apparatus via a network or a database system. This could be useful in particular if the tissue infiltration apparatus is incorporated into a laboratory control system. It is very generally conceivable that the order of two transport baskets is definably modifiable under the control of the laboratory control system—in remote-controlled fashion, so to speak. Control could also be applied to further preparation devices with a laboratory control system of this kind, so that ideally, almost entirely automated specimen preparation is possible. This kind of incorporation of the tissue infiltration apparatus or its control device could be achieved by linkage to a control computer for the laboratory control system via a network, or to a database system.

Tissue infiltration apparatuses 1 according to FIGS. 1 to 3 are incorporated, via network connection 32, into a laboratory control system (not shown in the Figures) that comprises a control computer and is linked to a database system in which patient data, among other information, is stored.

In conclusion, be it noted very particularly that the exemplifying embodiments discussed above serve merely to describe the teaching claimed, but do not limit it to the exemplifying embodiments.

PARTS LIST

1 Tissue infiltration apparatus
2 Input station
3 Output station
4 Transport basket
5 Cassettes
6 Transport apparatus
7 Liquid container
8 Means for definable modification of the order of multiple transport baskets
9 Storage unit
10 Control device
11 Liquid container serving for fixing
12 Fixing liquid
13 Liquid container serving for dehydration
14 Dehydration liquid
15 Liquid container serving for paraffin treatment
16 Paraffin
17 Switching station
18 Rail
19 Transport arm
20 Coupling element
21 Execution sequence
22 Control leads
23 Carousel
24 Receiving position of (23)
25 Input position of (23)
26 Output position of (23)
27 Transponder
28 Reading unit
29 Writing unit
30 Exchange apparatus
31 Heating unit
32 Network connection

What is claimed is:

1. A tissue infiltration apparatus for specimens present in cassettes carried by transport baskets, the tissue infiltration apparatus comprising:
    at least two liquid containers;
    a transport apparatus operable to transport at least two transport baskets in the tissue infiltration apparatus and deliver each transport basket to and from the liquid containers in a definable execution sequence, wherein a first of the at least two transport baskets has an initial execution sequence;
    at least one storage unit for storing at least one transport basket, wherein the storage unit does not contain liquid; and a control unit for controlling the tissue infiltration apparatus, wherein the control unit is configured to modify the initial execution sequence to create a modified execution sequence;

whereby the control unit causes the transport apparatus to deliver the first transport basket from the at least two liquid containers to the at least one storage unit to store the first of the at least two transport baskets according to the modified execution sequence while the second of the at least two baskets is delivered to one of the at least two liquid containers such that the second of the at least two baskets overtakes the first of the at least two baskets in the definable execution sequence.

2. The tissue infiltration apparatus according to claim 1, wherein the tissue infiltration apparatus comprises three liquid containers, each liquid container being capable of receiving one transport basket at a given time.

3. The tissue infiltration apparatus according to claim 2, wherein a first one of the liquid containers receives a liquid for fixing the specimens present in the cassettes, a second one of the liquid containers receives a liquid for dehydration of the specimens present in the cassettes, and a third one of the liquid containers receives paraffin for wax treatment of the specimens present in the cassettes.

4. The tissue infiltration apparatus according to claim 3, further comprising a heating unit associated with one of the liquid containers for applying energy to contents of the associated liquid containers.

5. The tissue infiltration apparatus according to claim 4, wherein the heating unit is associated with the third one of the liquid containers.

6. The tissue infiltration apparatus according to claim 1, wherein the transport apparatus includes at least one robot arm with which at least one transport basket is transportable in the tissue infiltration apparatus and to a location outside the tissue infiltration apparatus.

7. The tissue infiltration apparatus according to claim 1, wherein the storage unit is configured to store at least five transport baskets.

8. The tissue infiltration apparatus according to claim 1, wherein the transport apparatus is operable to deliver a first transport basket from a present position to the storage unit and then deliver a second transport basket to the position at which the first transport basket was located.

9. A tissue infiltration apparatus for specimens present in cassettes carried by transport baskets, the tissue infiltration apparatus comprising:

at least two liquid containers;

a transport apparatus operable to transport at least two transport baskets in the tissue infiltration apparatus and deliver each transport basket to and from the liquid containers in a definable execution sequence;

means for changing the order in which two transport baskets pass through the tissue infiltration apparatus by causing one of the two baskets to overtake the other of the two baskets as the two baskets are transported through the tissue infiltration apparatus; and a filling and draining unit associated with one of the at least two liquid containers for exchanging liquid in such container with a different liquid.

10. The tissue infiltration apparatus according to claim 9, wherein the means for changing the order of the transport baskets includes at least one storage unit configured to store at least one transport basket, and the storage unit is arranged at one of the liquid containers.

11. The tissue infiltration apparatus according to claim 9, further comprising a control device connected to the transport apparatus and to the filling and draining unit for controlling the transport apparatus and the filling and draining unit.

12. The tissue infiltration apparatus according to claim 11, wherein the control device is incorporated in a laboratory control system by linkage to a control computer for the laboratory control system via a network or to a database system.

13. The tissue infiltration apparatus according to claim 12, wherein the order of the two transport baskets is defined and changed under the control of the laboratory control system.

\* \* \* \* \*